(12) United States Patent
Heffernan

(10) Patent No.: US 6,562,979 B1
(45) Date of Patent: May 13, 2003

(54) PROCESS FOR THE PREPARATION OF SUBSTITUTED BENZISOTHIAZOLE COMPOUNDS

(75) Inventor: Gavin David Heffernan, Florence, NJ (US)

(73) Assignee: BASF Aktiengesellschaft, Ludwigshafen (DE)

(*) Notice: Subject to any disclaimer, the term of this patent is extended or adjusted under 35 U.S.C. 154(b) by 0 days.

(21) Appl. No.: 10/019,466

(22) PCT Filed: Jul. 10, 2000

(86) PCT No.: PCT/US00/18767

§ 371 (c)(1),
(2), (4) Date: Jul. 9, 2002

(87) PCT Pub. No.: WO01/05775

PCT Pub. Date: Jan. 25, 2001

Related U.S. Application Data

(63) Continuation-in-part of application No. 09/354,697, filed on Jul. 16, 1999, now abandoned.

(51) Int. Cl.⁷ ..................... C07D 275/04; C07D 401/00
(52) U.S. Cl. ........................................ 548/207; 544/310
(58) Field of Search ........................... 548/207; 544/310

(56) References Cited

U.S. PATENT DOCUMENTS

| | | | |
|---|---|---|---|
| 5,750,542 A | * 5/1998 | Villalobos et al. | 514/322 |
| 6,166,055 A | * 12/2000 | Widdowson et al. | 514/373 |
| 6,365,612 B2 | * 4/2002 | Genin et al. | 514/373 |

* cited by examiner

Primary Examiner—Deborah C. Lambkin
(74) Attorney, Agent, or Firm—Keil & Weinkauf

(57) ABSTRACT

A single-step process for the preparation of formula (I) benzisothiazoles from 2-acylphenylthiocyanates. Formula (I) benzisothiazoles are useful as key intermediates in the manufacture of herbicidally active compounds.

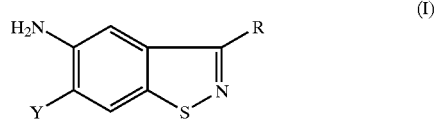

(I)

15 Claims, No Drawings

PROCESS FOR THE PREPARATION OF SUBSTITUTED BENZISOTHIAZOLE COMPOUNDS

This Application is a 371 of PCT/US06/18767 Jul. 10, 2000 which is a CIP of Ser. No. 09/354,697 Jul. 16, 1999 abandoned.

BACKGROUND OF THE INVENTION

Substituted-benzisothiazole herbicidal agents are described in U.S. Pat. No. 5,484,763 and WO 99/14216, among many other publications, and are highly desirable crop-selective components of good pesticide management programs. Said substituted-benzisothiazole herbicidal agents are prepared from benzisothiazole and heteroarylisothiazole compounds.

Methods to prepare benzisothiazole and heteroarylisothiazole compounds ("isothiazoles") are known in the literature. However, the only known single-step process requires harsh reaction conditions and affords maximum product yields of only 38%. This poor yield decreases markedly when the heteroarylisothiazole ring is substituted (Canadian Journal of Chemistry, 1973, 51, 1741). Such yields and reaction conditions are not amenable to large scale preparation or manufacturing conditions.

The two-step syntheses of said isothiazoles require the isolation of intermediates, resulting in undue solvent waste load on the environment. In addition, these syntheses require harsh reaction conditions, utilize expensive reagents and result in only marginally acceptable overall yields, even for relatively unsubstituted isothiazoles. (Journal of Chemical Research, Synop., 1979, 395 and Journal of the Chemical Society, Perkin II, 1977, 1114.)

Thus, it is an object of the present invention to provide a single-step process for the preparation of substituted benzisothiazole compounds which is amenable to large scale preparation.

It is another object of this invention to provide a means of obtaining a substituted benzisothiazole compound in good yield under relatively mild reaction conditions from readily available starting materials and reagents.

It is a further object of the invention to provide an environmentally sound commercial source of substituted benzisothiazole intermediates for the preparation of important substituted-benzisothiazole herbicidal agents.

SUMMARY OF THE INVENTION

There is provided a process for the preparation of a benzisothiazole compound of formula I

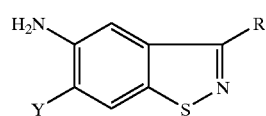

(I)

wherein
Y is hydrogen or halogen;
R is $CO_2R_3$, $C_1$–$C_6$alkyl optionally substituted with one or more halogen, $C_1$–$C_6$alkoxy, $CO_2R_1$ or $COR_2$ groups, or
a 6-membered heterocyclic ring optionally substituted with one or more halogen, CN, $NO_2$, $C_1$–$C_6$alkyl, $C_1$–$C_6$haloalkyl, $C_1$–$C_6$alkoxy or $C_1$–$C_6$haloalkoxy groups; and $R_1$, $R_2$ and $R_3$ are each independently hydrogen, $C_1$–$C_6$alkyl or $NH_2$ which process comprises reacting a compound of formula II

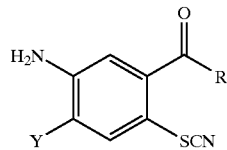

II wherein Y and R are as described hereinabove with an ammonia source in the presence of a solvent.

Also provided is a method for the use of the formula I compound in a process to manufacture herbicidally active substituted-benzisothiazole agents.

DETAILED DESCRIPTION OF THE INVENTION

The present invention provides a process for the single-step preparation of a substituted benzisothiazole compound from an appropriate 2-acylphenylthiocyanate precursor. Said benzisothiazole compounds are useful as key intermediates in the preparation of important herbicidal agents such as those described in U.S. Pat. No. 5,484,763 and WO 99/14216. Such herbicidal agents are critical to the production and quality of the global food supply. The efficient preparation of such herbicidally active compounds in an environmentally sound manner is a constant challenge.

The process of the invention provides a single step preparation of a substituted benzisothiazole compound of formula I, wherein formula I is as described hereinabove, from readily available starting materials and under relatively mild reaction conditions allowing effective large scale commercial production. Preferred formula I compounds prepared by the process of the present invention are those compounds wherein R is $C_1$–$C_6$alkyl or $CO_2R_3$, and $R_3$ is $C_1$–$C_6$alkyl. More preferred formula I compounds are those compounds wherein Y is hydrogen or F and R is $C_1$–$C_6$alkyl or $CO_2R_3$.

The term halogen as used in the specification and claims designates chlorine, fluorine, bromine or iodine. The term haloalkyl designates an alkyl group, $C_nH_{2n+1}$ which contains from one halogen atom to 2n+1 halogen atoms. The term, 6-membered heterocyclic ring, designates a 6-membered aromatic ring system containing one or two heteroatoms selected from O, N or S and which is connected through a carbon atom. Examples of 6-membered heterocyclic ring include: pyridine, pyrimidine, pyran, thiopyran or the like.

In accordance with the process of the invention, a benzisothiazole of formula I may be conveniently prepared by reacting an appropriately substituted 2-acylphenylthiocyanate of formula II with an ammonia source such as ammonia, ammonium hydroxide, an ammonium salt, for example ammonium chloride, ammonium acetate, ammonium trifluoroacetate or the like, or any of the conventional means of sourcing ammonia in the presence of a solvent, preferably a polar solvent. The reaction is illustrated in flow diagram I wherein Y and R are as described hereinabove.

Flow Diagram I

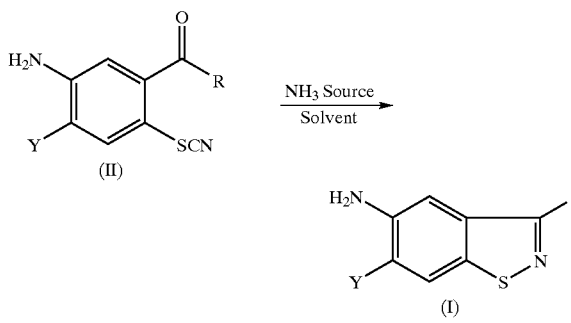

Formula II compounds may be readily prepared by conventional procedures such as the reaction of sodium thiocyanate with the appropriately substituted benzoyl compound of formula III in the presence of bromine and an acid. The reaction is illustrated in flow diagram II.

Flow Diagram II

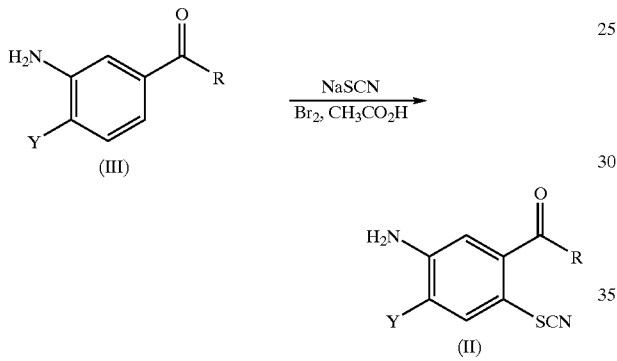

Solvents suitable for use in the process of the invention include polar solvents such as water, alcohols, organic acids, esters and aprotic solvents such as dioxane or acetonitrile. Preferred solvents are water, dioxane or lower alkyl alcohols, e.g. methanol, ethanol, propanol, isopropanol, or the like, or a mixture thereof.

The ammonia source may be any of the conventional means of introducing ammonia such as ammonia gas, ammonium hydroxide, ammonium salts or the like, preferably ammonium hydroxide or an ammonium salt. The ammonium salts operable in the inventive process are those salts which have sufficient solubility in the particular solvent employed. Examples of suitable ammonium salts include trifluoroacetate, acetate, nitrate, sulfamate, chloride, sulfate, and the like, preferably acetate or trifluoroacetate.

In the process of the invention, reaction temperature is directly related to reaction rate, thus increased temperatures lead to increased reaction rates. However, excessively high temperatures may lead to undesired side reactions and decreased product yield and purity. A suitable reaction temperature range may be about room temperature to the reflux temperature of the particular solvent used.

In actual practice, a 2-acylphenylthiocyanate compound of formula II is treated with an ammonia source, preferably ammonium hydroxide or an ammonium salt in the presence of a solvent, preferably a polar solvent, more preferably water, dioxane or a lower alkyl alcohol such as a $C_1$–$C_4$alkyl alcohol, e.g. methanol or isopropanol, or a mixture thereof, at a temperature range of about room temperature to the reflux temperature of the solvent. When the reaction is complete, the desired formula I benzisothiazole product is isolated using conventional procedures such as extraction, filtration, chromatography, or the like.

In the process of the invention, the amount of the ammonia source is not narrowly critical and amounts of about 1 to 5 molar equivalents, preferably about 1 to 3 molar equivalents, may be employed. It is to be understood, greater amounts of the ammonia source, i.e. greater than 5 molar equivalents, may be employed, however, no advantage may be gained.

The compounds of formula I are useful as intermediates in the manufacture of substituted-benzisothiazole herbicidal agents. Accordingly, in one embodiment of the invention, the formula I compound prepared from the formula II compound, as described hereinabove, may be reacted with a cyclic compound of formula IVa or IVb

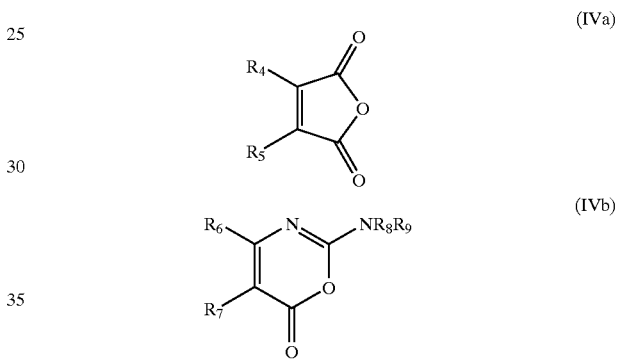

wherein $R_4$ and $R_5$ are each independently hydrogen, $C_1$–$C_6$alkyl, $C_1$–$C_6$haloalkyl, $C_3$–$C_6$cycloalkyl, $C_3$–$C_6$cyclohaloalkyl, or $R_4$ and $R_5$ may be taken together with the atoms to which they are attached to form a ring in which $R_4R_5$ represents a 5- or 6-membered cycloalkylene group which may be optionally substituted with one to three halogen or methyl groups;

$R_6$ and $R_7$ are each independently hydrogen, halogen, or $C_1$–$C_6$ haloalkyl;

$R_8$ and $R_9$ are each independently $C_1$–$C_4$alkyl in the presence of an acid or a base, optionally in the presence of a solvent, to form a compound of formula V or formula VI wherein $R_{10}$ is hydrogen;

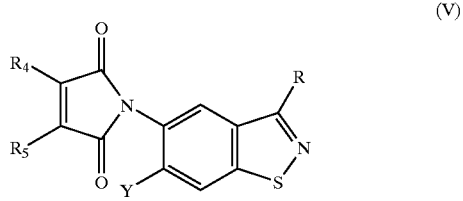

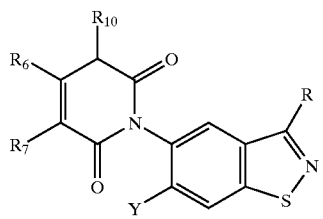

and in the case of VI, optionally further reacting VI with an $C_1$–$C_6$alkyl halide, $R_{11}X$, in the presence of a base to form a compound of formula VI wherein $R_{10}$ is $C_1$–$C_4$alkyl. The reaction is illustrated in flow diagram III wherein X or bromide.

Flow Diagram III

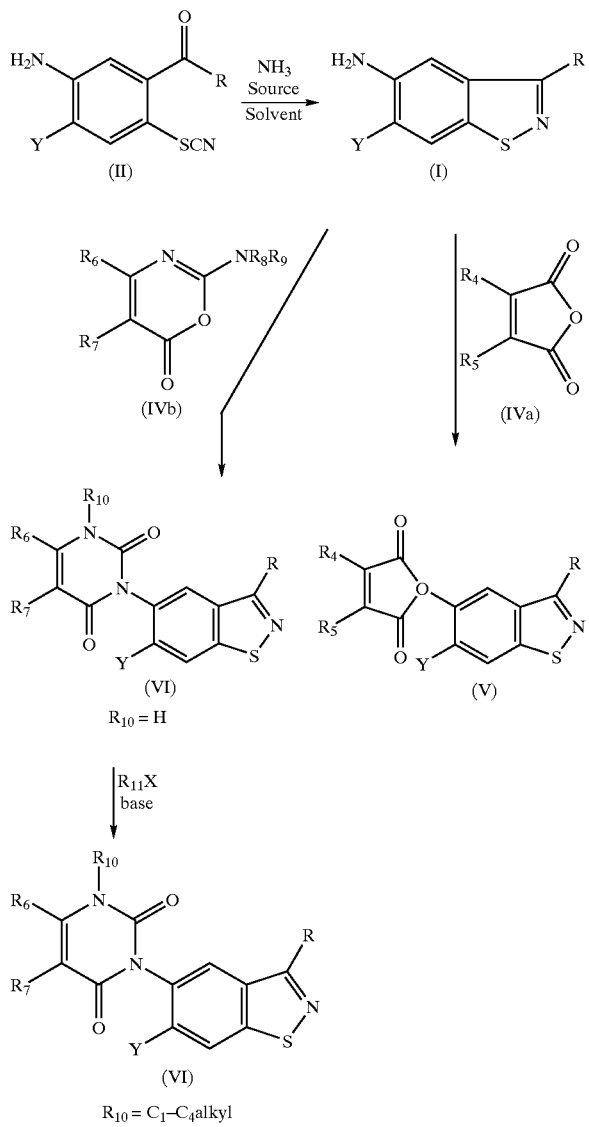

Among the methods known to convert compounds of formula I to the herbicidally active products of formula V and VI are those described in U.S. Pat. No. 5,484,763 and WO 99/14216.

In order to present a more clear understanding of the invention, the following examples are set forth below. These examples are merely illustrative, and are not to be understood as limiting the scope and underlying principles of the invention in any way.

The terms NMR and HPLC designate nuclear magnetic resonance and high performance liquid chromatography, respectively. Unless otherwise noted, all parts are parts by weight.

EXAMPLE 1

Preparation of 2-Acetyl-4-amino-5-fluorophenyl-thiocyanate

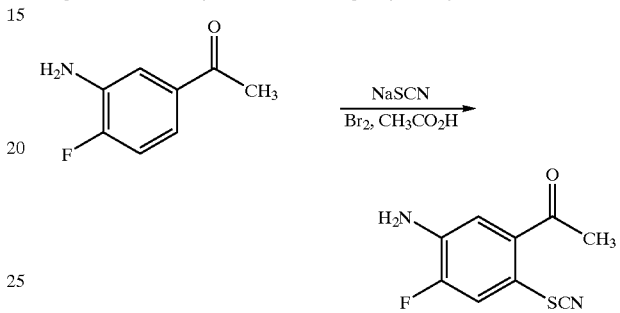

A 2M solution of bromine in acetic acid (32.7 ml, 65.4 mmol) is added dropwise to a stirred mixture of 4-acetyl-2-amino-fluorobenzene (5.0 g, 32.6 mmol) and sodium thiocyanate (7.94 g, 97.9 mmol) in glacial acetic acid. The reaction mixture is stirred at room temperature for one hour, poured into water and extracted with ethyl acetate. The extracts are combined, washed sequentially with water and brine, dried over magnesium sulfate, and concentrated in vacuo to afford the title compound as an orange solid, 4.68 g, 68% yield, identified by $^1$HNMR spectroscopy and HPLC analyses.

EXAMPLE 2

Preparation of 5-Amino-6-fluoro-3-methylbenzisothiazole

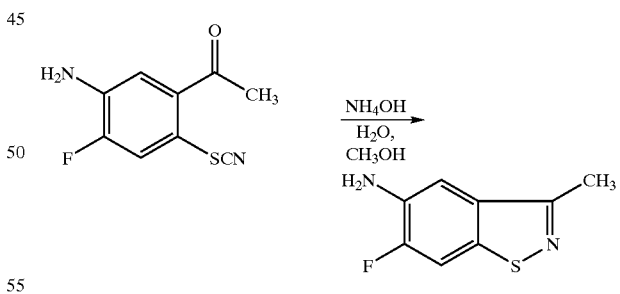

A solution of 2-acetyl-4-amino-5-fluorophenyl-thiocyanate (100 mg, 0.476 mmol) in methanol is treated with 30% ammonium hydroxide (4 ml) and stirred for 42 hours. The reaction mixture is poured into water and extracted with ethyl acetate. The extracts are combined, washed with brine, dried over magnesium sulfate and concentrated in vacuo to give an oil. The oil is chromatographed (silica gel/hexane-ethyl acetate as eluant) to afford the title product as an orange solid, 36.9 mg, 56% yield, identified by $^1$HNMR sepctroscopy and HPLC analyses.

EXAMPLE 3

Preparation of 3-Amino-4-fluoro-6-thiocyanotophenyl 2-(3-methylpyridyl) ketone

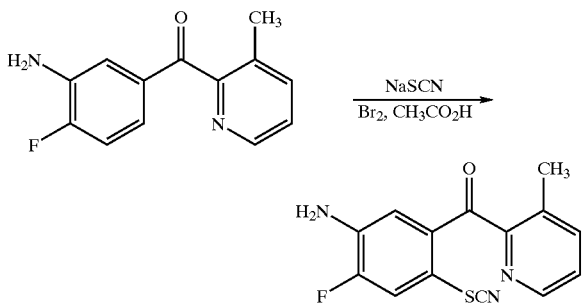

A 2 M solution of bromine in acetic acid (12 ml, 0.024 mol) is added dropwise to a stirred mixture of 3-amino-4-fluorophenyl 2-(3-methylpyridyl)ketone (4.20 g, 0.017 mol) and sodium thiocyanate (4.15 g, 0.051 mol) in glacial acetic acid and stirred at room temperature for one hour. The reaction mixture is poured into a cold solution of aqueous ammonia, and filtered. The filtercake is dried over calcium sulfate in a vacuum oven to afford the title compound as a yellow solid, 4.19 g, 80% yield, identified by $^1$H, $^{13}$C and $^{19}$FNMR and mass spectral analyses.

EXAMPLE 4

Preparation of 5-Amino-6-fluoro-3-(3-methyl-2-pyridyl)-benzoisothiazole

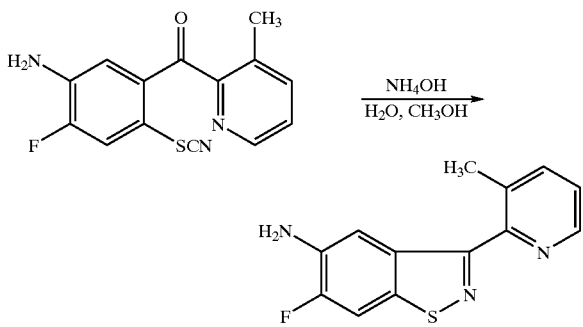

A mixture of 3-amino-4-fluoro-6-thiocyanatophenyl 2-(3-methylpyridyl)ketone (2.74 g, 0.01 mol) and 30% ammonium hydroxide in methanol is stirred overnight at room temperature, diluted ten-fold with equal amounts of methanol and 30% ammonium hydroxide solution and filtered. The filtercake is dried to afford the title compound as a yellow solid, 1.31 g, 51% yield, identified by $^1$H, $^{13}$C and $^{19}$FNMR and mass spectral analyses.

EXAMPLE 5

Preparation of Ethyl (5-Amino-4-fluoro-2-thiocyanotophenyl)-glyoxylate

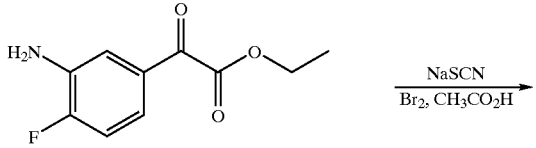

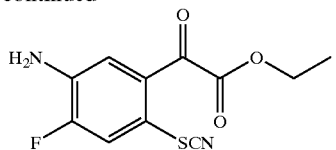

A solution of ethyl (5-amino-4-fluorophenyl)glyoxylate (90 g. 0.426 mol) and sodium thiocyanate (114 g, 1.41 mol) in acetic acid is treated dropwise with a 2M solution of bromine in acetic acid (980 ml, 0.98 mmol), and stirred for 1 hour. The reaction mixture is poured into ice and extracted with ethyl acetate. The extracts are combined, washed sequentially with water and brine, dried over magnesium sulfate, and concentrated in vacuo to give an oil residue. The residue is purified via flash chromatography (silica gel/hexane-ethylacetate as eluant) to afford the title product as a yellow solid, 60 g, 52% yield, identified by $^1$HNMR analysis.

EXAMPLE 6

Preparation of Ethyl 5-Amino-6-fluoro-1,2-benzisothiozole-3-carboxylate

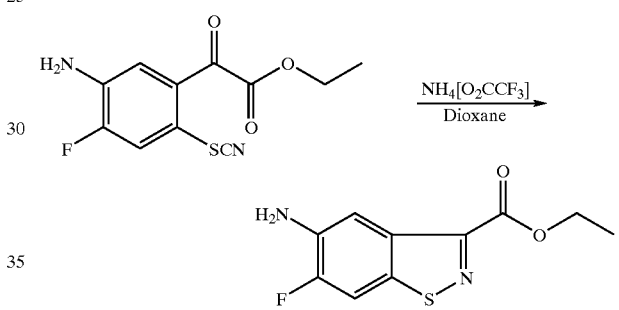

A solution of ethyl (5-amino-4-fluoro-2-thiocyanatophenyl)glyoxylate (1.00 g, 3.73 mmol) in dioxane, under nitrogen, is treated with ammonium trifluoroacetate (1.71 g, 13 mmol) and heated at reflux temperature for 2 hours. The crude reaction mixture is chromatographed (silica gel/hexane-ethylacetate as eluant) to afford the title product as a light green solid, 0.59 g, 66% yield, identified by $^1$HNMR analysis.

EXAMPLE 7

Preparation of 5-Amino-3-substituted-benzisothiazole

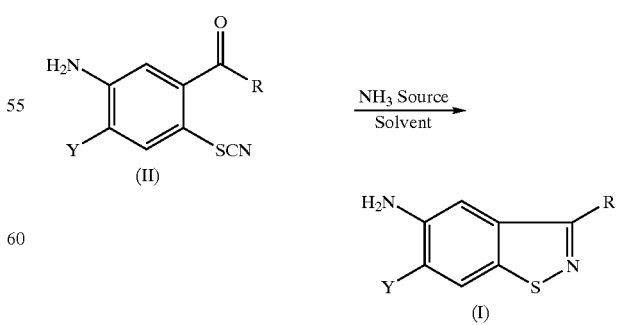

Using essentially the same procedures described hereinabove and employing the appropriate 2-acylphenylthiocyanate substrate, the compounds shown in Table I are obtained.

TABLE I

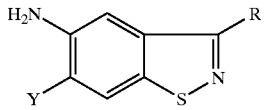

(I)

| R | Y | Ammonia Source | Solvent | mp °C. | % yield |
|---|---|---|---|---|---|
| CH₂OCH₃ | F | NH₄O₂CCF₃ | Dioxane | 88–90 | 37 |
| 2-pyridyl | F | NH₄OH | Methanol |  | 40 |
| CH₃CH₂ | F | NH₄OH | Dioxane |  |  |

What is claimed is:

1. A process for the preparation of a compound of formula I

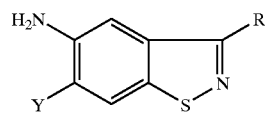

(I)

wherein
  Y is hydrogen or halogen;
  R is $CO_2R_3$, $C_1$–$C_6$alkyl optionally substituted with one or more halogen, $C_1$–$C_6$alkoxy, $CO_2R_1$ or $COR_2$ groups, or
    a 6-membered heterocyclic ring optionally substituted with one or more halogen, CN, $NO_2$, $C_1$–$C_6$alkyl, $C_1$–$C_6$haloalkyl, $C_1$–$C_6$alkoxy or $C_1$–$C_6$halo-alkoxy groups; and
  $R_1$, $R_2$ and $R_3$ are each independently hydrogen, $C_1$–$C_6$alkyl or $NH_2$
which process comprises reacting a compound of formula II

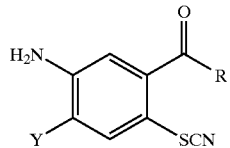

(II)

wherein Y and R are as described above, with an ammonia source in the presence of a solvent.

2. The process according to claim 1 wherein the solvent comprises dioxane.

3. The process according to claim 1 wherein the solvent comprises water or a $C_1$–$C_4$alkyl alcohol or a mixture thereof.

4. The process according to claim 1 wherein the ammonia source is ammonium hydroxide or ammonium salt.

5. The process according to claim 4 wherein the ammonium salt is ammonium trifluoracetate or ammonium acetate.

6. The process according to claim 1 having a formula I compound wherein Y is hydrogen or F.

7. The process according to claim 1 having a formula I compound wherein R is $C_1$–$C_6$alkyl or $CO_2R_3$; and $R_3$ is $C_1$–$C_4$alkyl.

8. The process according to claim 5 wherein the solvent is selected from the group consisting of water, a $C_1$–$C_4$alkyl alcohol, a mixture of water and a $C_1$–$C_4$alkyl alcohol, and dioxane.

9. The process according to claim 8 having a formula I compound wherein Y is hydrogen or F.

10. The process according to claim 9 having a formula I compound wherein R is $C_1$–$C_6$alkyl or $CO_2R_3$; and $R_3$ is $C_1$–$C_4$alkyl.

11. A process according to claim 1 further comprising the preparation of a compound of formula V or formula VI

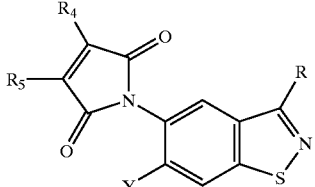

(V)

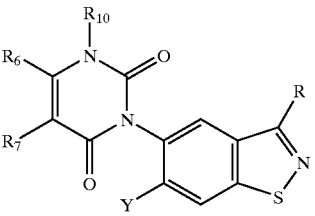

(VI)

wherein

Y is hydrogen or halogen;

R is $CO_2R_3$, $C_1$–$C_6$alkyl optionally substituted with one or more halogen, $C_1$–$C_6$alkoxy, $CO_2R_1$, or $COR_2$ groups, or
  a 6-membered heterocyclic ring optionally substituted with one or more halogen, CN, $NO_2$, $C_1$–$C_6$alkyl, $C_1$–$C_6$haloalkyl, $C_1$–$C_6$alkoxy or $C_1$–$C_6$haloalkoxy groups; and $R_1$, $R_2$ and $R_3$ are each independently hydrogen, $C_1$–$C_6$alkyl or $NH_2$ $R_4$ and $R_5$ are each independently hydrogen, $C_1$–$C_6$alkyl, $C_1$–$C_6$haloalkyl, $C_3$–$C_6$cycloalkyl, $C_3$–$C_6$cyclohaloalkyl, or $R_4$ and $R_5$ may be taken together with the atoms to which they are attached to form a ring in which $R_4R_5$ represents a 5- or 6-membered cycloalkylene group which may be optionally substituted with one to three halogen or methyl groups;

$R_6$ and $R_7$ are each independently hydrogen, halogen, or $C_1$–$C_6$ haloalkyl;

$R_8$ and $R_9$ are each independently $C_1$–$C_4$alkyl; and $R_{10}$ is hydrogen or $C_1$–$C_4$alkyl, by reacting the formula I compound with a compound of formula IVa or IVb

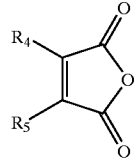

(IVa)

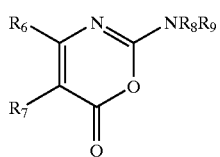
(IVb)

wherein $R_4$, $R_5$, $R_6$, $R_7$, $R_8$ and $R_9$ are as described hereinabove in the presence of an acid or a base, optionally in the presence of a solvent to form the desired compound of formula V or formula VI wherein $R_{10}$ is hydrogen, optionally in the case of the formula VI compound reacting said compound with a $C_1$–$C_4$alkylhalide, $R_{11}X$, wherein $R_{11}$ is $C_1$–$C_4$alkyl and X is chloride or bromide in the presence of a base to give the formula VI compound wherein $R_{10}$ is $C_1$–$C_4$alkyl.

12. The process according to claim 11 wherein the ammonia source is ammonium hydroxide, ammonium acetate or ammonium trifluoroacetate.

13. The process according to claim 11 wherein the solvent is dioxane, water, a $C_1$–$C_4$alkyl alcohol or a mixture of water and a $C_1$–$C_4$alkyl alcohol.

14. The process according to claim 11 wherein Y is F; R is $C_1$–$C_6$alkyl or $CO_2R_3$; $R_3$ is $C_1$–$C_4$alkyl; $R_6$ and $R_7$ are each independently hydrogen or $CF_3$; and $R_{10}$ is $C_1$–$C_4$alkyl.

15. The process according to claim 14 wherein a formula VI compound is prepared.

* * * * *